United States Patent
McLean et al.

(12) 
(10) Patent No.: US 6,300,329 B1
(45) Date of Patent: Oct. 9, 2001

(54) PHARMACEUTICAL AGENTS FOR THE TREATMENT OF PARKINSON'S DISEASE, ADHD AND MICROADENOMAS

(76) Inventors: Stafford McLean, 368 Mistuxet Ave., Stonington, CT (US) 06378; Steven H. Zorn, 62C Patricia Ave., North Stonington, CT (US) 06359-1036; Elisa R. Jackson, 36 Case St., Norwich, CT (US) 06360-2215

( * ) Notice: Subject to any disclaimer, the term of this patent is extended or adjusted under 35 U.S.C. 154(b) by 0 days.

(21) Appl. No.: 09/400,659

(22) Filed: Sep. 21, 1999

Related U.S. Application Data

(60) Provisional application No. 60/103,868, filed on Oct. 12, 1998, and provisional application No. 60/101,191, filed on Sep. 21, 1998.

(51) Int. Cl.⁷ .......................... A61K 31/50; A61K 31/495
(52) U.S. Cl. ............................. 514/249; 514/878; 514/879
(58) Field of Search ................................... 514/249, 878, 514/879

(56) References Cited

U.S. PATENT DOCUMENTS

| | | | |
|---|---|---|---|
| 5,281,607 | 1/1994 | Stone | 514/280 |
| 5,616,585 | 4/1997 | Bright | 514/249 |

FOREIGN PATENT DOCUMENTS

| | | |
|---|---|---|
| 9528933 | 11/1995 | (WO) . |

OTHER PUBLICATIONS

Chemical Abstracts 123:143898, "Preparation of Heterotetracyclic Compounds as Dopamine Agonists", Oct. 1994.*
Chemical Abstracts 125:25806, "Treatment of Prolactin-Secrting Macroadenomas", Jun. 1996*
Jackson, D.M. et al., *Naunyn–Schiedebergs Archives of Pharmacology*, vol. 351, No. 2, 1995 pp. 146–155, "Time course of bromocriptine induced excitation in the rat: behavioral nad biochemical studies".
Prakash, C. et al. *Drug Metabolism and Disposition*, vol. 26, No. 5, 1998, pp. 448–456, "Metabolism and excretion of a new anxiolytic drug candidate, CP–93,393, in healthy male volunteers".
Search Report for PCT/IB99/01503 (1999).

* cited by examiner

*Primary Examiner*—Frederick Krass

(57) ABSTRACT

The present invention is directed to the use of certain pyrido[1,2-a]-pyrazine derivatives, also described as bis-azabicyclic compounds and defined by the formula (I) herein, in the treatment of Parkinson's disease, attention deficit hyperactivity disorder and microadenomas in mammals, and to related compositions.

5 Claims, 1 Drawing Sheet

PHARMACEUTICAL AGENTS FOR THE TREATMENT OF PARKINSON'S DISEASE, ADHD AND MICROADENOMAS

This application claims priority under 35 U.S.C. §119 U.S. application Ser. No. 60/101,191, filed Sep. 21, 1998, and Ser. No. 60/103,868, filed Oct. 12, 1998 which applications are hereby incorporated by reference.

FIELD OF THE INVENTION

The present invention is directed to the use of certain pyrido[1,2-a]-pyrazine derivatives, also described as bis-azabicyclic compounds, in the treatment of Parkinson's disease, attention deficit hyperactivity disorder ("ADHD") and microadenomas in mammals, including humans. It is also directed to the use of a dopamine-2 (D2) receptor agonist in combination with a serotonin-1A ($5HT_{1A}$) receptor agonist for the treatment for Parkinson's Disease. It is also directed to the use of an alpha-2 ($\alpha_2$) adrenergic receptor ligand in combination with either a D2 receptor agonist or a $5HT_{1A}$ receptor agonist for the treatment of ADHD. It is also directed to the use of a D2 receptor agonist in combination with a $5HT_{1A}$ receptor agonist for the treatment of ADHD. It is also directed to the use of an alpha-2 ($\alpha_2$) adrenergic receptor ligand in combination with both a D2 receptor agonist and a $5HT_{1A}$ receptor agonist for the treatment of ADHD.

BACKGROUND OF THE INVENTION

Serotonin plays a role in several psychiatric disorders, including anxiety, Alzheimer's disease, depression, nausea and vomiting, eating disorders, and migraine. (See Rasmussen et al., "Chapter 1. Recent Progress in Serotonin $(5HT)_{1A}$ Receptor Modulators", in *Annual Reports in Medicinal Chemistry*, Section I, 30, pp. 1–9, 1995, Academic Press, Inc.; Antigas et al., *Trends Neurosci.*, 19 (9), 1996, pp. 378–383; and Wolf et al., *Drug Development Research*, 40, 1997, pp. 17–34.) Serotonin also plays a role in both the positive and negative symptoms of schizophrenia. (See Sharma et al., *Psychiatric Annals.*, 26 (2), February, 1996, pp. 88–92.) Serotonin 1A receptor agonists have been shown to increase prefrontal cortex dopamine (DA) release. See Wedzony et al., *Eur. J. Pharmacol.*, 305: 73–78 (1996). Buspirone, a $5HT_{1A}$ receptor agonist, has been shown to be efficacious in treating a variety of symptoms associated with ADHD. Serotonin 1A receptor agonists have also been shown to reverse neuroleptic induced dystonia in nonhuman primates, a condition that mimics symptoms of human Parkinson's disease. See Casey, D. E., *Neuropsychopharmacol.*, 10:370S (1994).

Symptoms associated with ADHD have been shown to be relieved by catecholamine releasing drugs such as inethylphenidate, and by postsynaptic α2 adrenergic receptor agonists such as clonidine. Also, presynaptic α2 adrenergic receptor antagonists have been shown to increase norepinephrine (NE) release.

A number of 1-(2-pyrimidinyl)-4-[4-(cyclic-imido)butyl] piperidine derivatives have been disclosed as anxiolytic agents which are generally lacking sedative activity. Among these are buspirone, where the cyclic-imido group is 4,4-tetramethylene-piperidine-2,6-dion-1-yl (Wu et al., U.S. Pat. Nos. 3,717,634 and 3,907,801); Casten et al., U.S. Pat. No. 4,182,763); gepirone, where the group is 4,4-dimethylpiperidine-2,6-dion-1-yl (Temple, Jr., U.S. Pat. No. 4,423,049); and ipsapirone, where the group is 1,1-dioxobenzo[d] isothiazol-3(2H)-on-yl (Dompert et al., German patent publication 3,321,969-A1). See also Ishizumi et al., U.S. Pat. Nos. 4,507,303 and 4,543,55; Freed et al., U.S. Pat. No. 4,562,255; Stack et al., U.S. Pat. No. 4,732,983; New et al., U.S. Pat. No. 4,524,026; and Stack, U.S. Pat. No. 4,788,290.

Compounds of the formula (I) below are disclosed in U.S. Pat. No. 5,122,525 as useful for the treatment of anxiety and depression. The use of such compounds for the treatment of addiction is described in U.S. Pat. No. 5,616,885.

SUMMARY OF THE INVENTION

This invention relates to a method of treating a disorder selected from Parkinson's disease, ADHD, and microadenomas in a mammal, including a human, comprising administering to a mammal in need of such treatment an amount of a compound of the formula

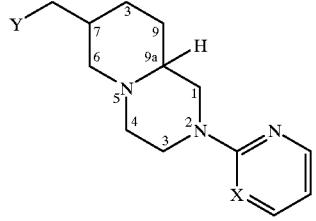

I or a pharmaceutically acceptable acid addition salt thereof, wherein
X is N or CH;
Y is

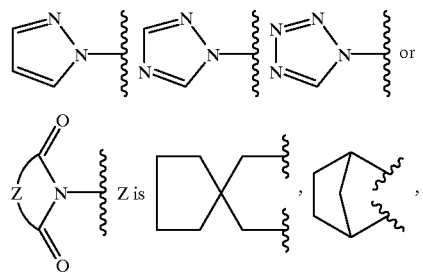

$SCH_2$, $OCH_2$, $Y^1(CH_2)_n$ or $Y^1(CH_2)_n$ substituted on carbon with up to 2 methyl groups;
n is 1 or 2; and
$y^1$ is $CH_2$, NH or $NCH_3$;
that is effective in treating such disorder.

In the compounds of the formula (I), Y is preferably

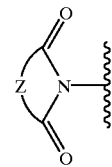

A particularly preferred compound is that wherein Z is $Y^1(CH_2)_n$, $Y^1$ is $CH_2$, n is 1 and X is N.

The compounds of formula I are D2 receptor agonists and useful in the treatment of Parkinson's disease. They also exhibit $5HT_{1A}$ receptor agonist activity.

The compounds of formula I also exhibit activity as $\alpha_2$ adrenergic receptor antagonists and are useful in treatment of ADHD. The compounds increase hippocampal NE release and also increase prefrontal cortex DA release.

The compounds of the formula I that are basic can form acid addition salts with a variety of organic and inorganic acids. The acids that can be used to prepare the pharmaceutically acceptable acid addition salts of the aforementioned base compounds of the formula I are those which form non-toxic acid addition salts, i.e., salts containing pharmacologically acceptable anions, such as the hydrochloride, hydrobromide, hydroiodide, nitrate, sulfate, bisulfate, phosphate, acid phosphate, acetate, lactate, citrate, acid citrate, tartrate, bitartrate, succinate, maleate, fumarate, gluconate, saccharate, benzoate, methanesulfonate, ethanesulfonate, benzenesulfonate, p-toluenesulfonate and pamoate [i.e., 1,1'-methylene-bis-(2-hydroxy-3-naphthoate)]salts.

The term "treating" as used herein, refers to reversing, alleviating, inhibiting the progress of, or preventing the disorder or condition to which such term applies, or one or more symptoms of such disorder or condition. The term "treatment", as used herein, refers to the act of treating, as "treating" is defined immediately above.

This invention also relates to a method for treating Parkinson's Disease in a mammal, including a human, comprising administering to a mammal in need of such treatment a D2 receptor agonizing agent in combination with a $5HT_{1A}$ receptor agonizing agent, wherein the two foregoing active agents are present in amounts such that the combination of such agents is effective in treating Parkinson's Disease.

This invention also relates to a pharmaceutical composition for treating Parkinson's disease in a mammal, including a human, comprising: (a) a D2 receptor agonizing agent or a pharmaceutically acceptable salt thereof; (b) a $5HT_{1A}$ receptor agonizing agent or pharmaceutically acceptable salt thereof; and (c) a pharmaceutically acceptable carrier; wherein the foregoing two active agents are in the composition in amounts such that the combination of such agents is effective in treating Parkinson's disease.

This invention also relates to a method of treating ADHD in a mammal, including a human, comprising administering to a mammal in need of such treatment an $\alpha_2$ adrenergic receptor ligand, or pharmaceutically acceptable salt thereof, in combination with either a D2 receptor agonizing agent or a $5HT_{1A}$ receptor agonizing agent, or pharmaceutically acceptable salt thereof, wherein the foregoing two active agents are present in amounts such that the combination of such active agents is effective in treating ADHD.

This invention also relates to a pharmaceutical composition for treating ADHD in a mammal, including a human, comprising: (a) an $\alpha_2$ adrenergic receptor ligand or a pharmaceutically acceptable salt thereof; (b) a D2 receptor agonizing agent or a $5HT_{1A}$ receptor agonizing agent, or a pharmaceutically acceptable salt thereof; and (c) a pharmaceutically acceptable carrier; wherein the two foregoing active agents are present in the composition in amounts such that the combination of such agents is effective in treating ADHD.

This invention also relates to a method of treating ADHD in a mammal, including a human, comprising administering to a mammal in need of such treatment a D2 receptor agonizing agent, or pharmaceutically acceptable salt thereof, in combination with a $5HT_{1A}$ receptor agonizing agent, or pharmaceutically acceptable salt thereof, wherein the foregoing two active agents are present in amounts such that the combination of such active agents is effective in treating ADHD.

This invention also relates to a pharmaceutical composition for treating ADHD in a mammal, including a human, comprising: (a) a D2 receptor agonizing agent or a pharmaceutically acceptable salt thereof; (b) a $5HT_{1A}$ receptor agonizing agent or a pharmaceutically acceptable salt thereof; and (c) a pharmaceutically acceptable carrier; wherein the two foregoing active agents are present in the composition in amounts such that the combination of such agents is effective in treating ADHD.

This invention also relates to a method of treating ADHD in a mammal, including a human, comprising administering to a mammal in need of such treatment an $\alpha_2$ adrenergic receptor ligand, or pharmaceutically acceptable salt thereof, in combination with a D2 receptor agonizing agent, or pharmaceutically acceptable salt thereof, and also a $5HT_{1A}$ receptor agonizing agent, or pharmaceutically acceptable salt thereof, wherein the three foregoing active agents are present in amounts such that the combination of such active agents is effective in treating ADHD.

This invention also relates to a pharmaceutical composition for treating ADHD in a mammal, including a human, comprising: (a) an $\alpha_2$ adrenergic receptor ligand or a pharmaceutically acceptable salt thereof; (b) a D2 receptor agonizing agent or a pharmaceutically acceptable salt thereof; (c) a $5HT_{1A}$ receptor agonizing agent or a pharmaceutically acceptable salt thereof; and (d) a pharmaceutically acceptable carrier; wherein the foregoing three active agents are present in the composition in amounts such that the combination of such agents is effective in treating ADHD.

Compounds of the formula I may contain chiral centers and therefore may exist in different enantiomeric and diastereomic forms. The term "compounds of the formula I", as used herein, refers to all optical isomers and all other stereoisomers of compounds of the formula I, as defined above, and to all racemic and other mixtures thereof, and to all pharmaceutical compositions and methods of treatment defined above that contain or employ such isomers or mixtures.

Formula I above includes compounds identical to those depicted but for the fact that one or more hydrogen or carbon atoms are replaced by isotopes thereof. Such compounds are useful as research and diagnostic tools in metabolism pharmacokinetic studies and in binding assays. Specific applications in research include radioligand binding assays, autoradiography studies and in vivo binding studies.

Examples of D2 receptor agonizing agents that can be used in the methods of this invention include, but are not limited to, compounds of the formula I and the pharmaceutically acceptable salts, pergolide, bromocriptane, ropinerol, and pramipexole.

Examples of $5HT_{1A}$ receptor agonizing agents that can be used in the methods of this invention include, but are not limited to: (a) compounds of the formula I and their pharmaceutically acceptable salts, (b) buspirone (U.S. Pat. Nos. 3,717,638; 3,907,801 and 4,182,763); (c) gepirone (U.S. Pat. No. 4,423,049); (c) ipsapirone (German patent publication 3,321,969-A1); and (d) and flexinoxan.

Examples of $\alpha_2$ adrenergic receptor antagonizing agents that can be used in the methods of this invention include, but are not limited to, compounds of the formula I and their pharmaceutically acceptable salts, yohimbine and idazoxan.

Examples of more specific embodiments of this invention are the above methods of treating ADHD and pharmaceutical compositions for the treatment of ADHD that employ an $\alpha_2$ adrenergic receptor ligand wherein such ligand is a presynaptic $\alpha_2$ adrenergic receptor antagonist or a post synaptic $\alpha_2$ adrenergic receptor agonist.

A preferred method of this invention is a method of treating Parkinson's Disease in a mammal, including a human, comprising administering to a mammal in need of such treatment an amount of the following compound of the formula I shown below:

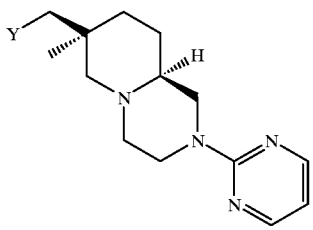

i.e., wherein X is nitrogen, wherein Y is a group of the formula

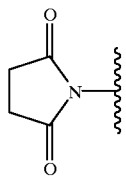

("sunipetron"), or pharmaceutically acceptable salt thereof, that is effective in treating Parkinson's Disease.

Another preferred embodiment of this invention is a method for treating ADHD in a mammal including a human, comprising administering to a mammal in need of such treatment an amount of sunipetron, or pharmaceutically acceptable salt thereof, that is effective in treating ADHD.

Another preferred method of this invention is a method for treating microadenomas in a mammal including a human, comprising administering to a mammal in need of such treatment an amount of sunipetron, or pharmaceutically acceptable salt thereof, that is effective in treating microadenomas.

DETAILED DESCRIPTION OF THE INVENTION

Figure 1:
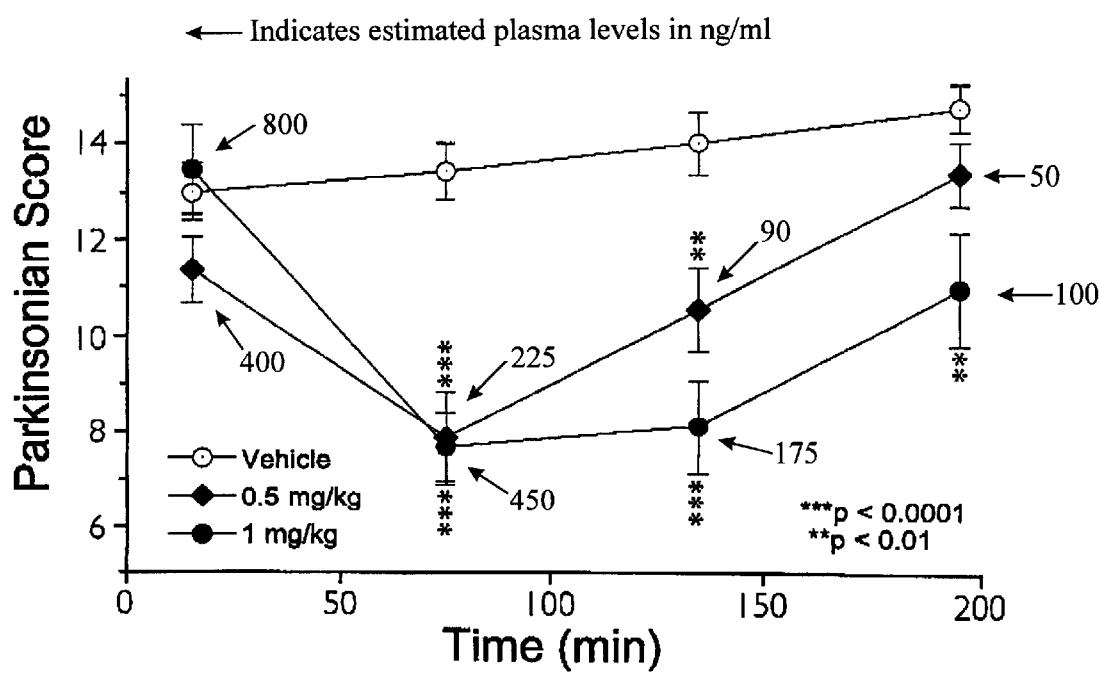
FIG. 1 shows parkinsonian scores obtained in monkeys treated with either 0.5 mg/kg or 1.0 mg/kg of a compound of formula I.

All patents, patent applications, and articles listed herein are hereby incorporated by reference in their entireties Compounds of the formula I and their pharmaceutically acceptable salts may be prepared as described in U.S. Pat. Nos. 5,122,525, 5,185,449, 5,455,350, U.S. patent application Ser. No. 08/470,377, now abandoned which was filed on Jun. 6, 1995, and World Patent Application PCT/IB97/00704, which designates the United States and was filed on Jun. 16, 1997.

The compounds of the formula I are capable of forming a wide variety of different salts with various inorganic and organic acids. The acids that can be used to prepare the pharmaceutically acceptable acid addition salts of the base compounds of this invention are those which form non-toxic acid addition salts, i.e., salts containing pharmacologically acceptable anions, such as hydrochloride, hydrobromide, hydroiodide, nitrate, sulfate or bisulfate, phosphate or acid phosphate, acetate, lactate, citrate or acid citrate, tartrate or bitartrate, succinate, maleate, fumarate, gluconate, saccharate, benzoate, methanesulfonate and pamoate [i.e., 1,1'-methylene-bis-(2-hydroxy-3-naphthoate)] salts. Although such salts must be pharmaceutically acceptable for administration to animals, it is often desirable in practice to initially isolate a compound of the formula I from the reaction mixture as a pharmaceutically unacceptable salt and then simply convert the latter back to the free base compound by treatment with an alkaline reagent, and subsequently convert the free base to a pharmaceutically acceptable acid addition salt. The acid addition salts of the base compounds of this invention are readily prepared by treating the base compound with a substantially equivalent amount of the chosen mineral or organic acid in an aqueous solvent medium or in a suitable organic solvent such as methanol or ethanol. Upon careful evaporation of the solvent, the desired solid salt is obtained.

For use in treating Parkinson's disease, ADHD or microadenomas in a human subject, a compound of the formula I, or a pharmaceutically-acceptable salt thereof, is administered in an amount of about 2–300 mg/day, in single or divided daily doses. In particular cases, dosages outside that range are prescribed at the discretion of the attending physician. The preferred route of administration is generally oral, but parenteral administration (es, intramuscular, intravenous, intradermal) will be preferred in special cases, e.g., where oral absorption is impaired as by disease, or the patient is unable to swallow. In one embodiment, the compound of formula I is administered in an individual dosage of about 1.0 mg/kg at a frequency of about three times per day. A controlled-release formulation can be employed instead that is administered once per day. In another embodiment, the compound is administered in an amount required by the particular route of administration to achieve a plasma concentration of between 100 and 500 ng/ml, preferably about 200 ng/ml, at between 2 and 3 hours following administration.

The compounds used in the present invention are generally administered in the form of pharmaceutical compositions comprising at least one of the compounds of the formula (I), or a salt thereof, together with a pharmaceutically acceptable vehicle or diluent. Such compositions are generally formulated in a conventional manner utilizing solid or liquid vehicles or diluents as appropriate to the mode of desired administration: for oral administration, in the form of tablets, hard or soft gelatin capsules, suspension, granules, powders and the like; and, for parenteral administration, in the form of injectable solutions or suspensions, and the like.

Binding of a compound to the D2 receptor can be determined using the follow D2 receptor binding assay.

$LTK^-$ cells expressing the human $D_2$ long ($D_{2L}$) receptor are grown (T-1 75 flasks) in D-glucose containing minimal essential media (DMEM, Gibco) supplemented with 10% fetal bovine serum (FBS). The cells are dislodged with 5 mM EDTA in PBS and homogenized in 50 mM Tris HCl (pH 7.4) with 5 mM $MgSO_4$, using a Brinkman Polytron at setting 6 for 20 sec. Membranes are recovered after multiple rounds of separation by centrifugation and resuspension in fresh ice-cold buffer. The tissue (~2 mg tissue, wet weight) is added to test tubes containing incubation buffer (50 mM Tris HCl, 120 mM NaCl, 2 mM $MgCl_2$, 5 mM KCl, 5 mM $CaCl_2$, pH 7.2), various concentrations of test drug, and [$^3$H]-spiperone (0.06 nM final concentration, Amersham, Arlington Heights Ill.). Non-specific binding is determined in the presence of 2 uM (+)-butaclamol. After 45 min at 30°

C., incubations are terminated by rapid filtration through Whatman GF/B filters using a Brandel cell harvester. The membranes are washed using 3×4 ml of ice-cold buffer and membrane-bound ligand is determined by liquid scintillation counting of the filters in Ready-Safe scintillation cocktail (for tritiated ligands). The $K_d$(0.06 nM) for the radioligand is determined previously by saturation analysis and used to calculate apparent $K_i$'s by means of the Cheng-Prusoff equation.

The agonist or antagonist activity of a compound at the D2 receptor can be determined using the following three assays.

(1) Human $D_2$ receptor modulation of cAMP formation in $GH_4C_1$ cells $GH_4C_1$ cells, derived from rat pituitary, expressing either the long or short forms of the human $D_2$ receptor, are grown to confluence in (HAM) F-10 Nutrient Mixture (Gibco) supplemented with 10% FBS and 2 mM I-glutamine and 10 U/ml penicillin-streptomycin in T-175 flasks. The cells are dislodged with 5 mM ethylenediamine tetraacetic acid (EDTA) in phosphate buffered saline (PBS) and resuspended in PBS containing 5 mM $MgCl_2$, 30 mM hydroxyethylpiperizine-N-ethanesulfonic acid (HEPES), and 50 mM isobutyl methyl xanthine (IBMX). Cells (~200,000/tube) are exposed to 5 mM forskolin, 100 nM quinpirole or forskolin plus quinpirole plus antagonist for 11 minutes. In experiments with antagonists, cells are exposed to the antagonists 11 minutes prior to quinpirole challenge. To judge agonist activity, the effect of a compound on forskolin stimulated cAMP accumulation is tested in the absence of the agonist quinpirole. The reaction is terminated with the addition of 6N perchloric acid, and samples are neutralized with 5N potassium hydroxide and 2 M Tris buffer. Cyclic AMP levels are measured using a commercially available competitive binding kit (Amersham). $IC_{50}$ values are calculated by linear regression analysis of the concentration-response curves. Apparent $K_i$ values are calculated using the equation: $K_i = IC_{50}/(1+[\text{agonist}]/[\text{agonist } EC_{50}])$.

(2) Electrophysiology in Rat Brain Slices

Male Sprague-Dawley rats (200–250 gm, Charles River Laboratories, Wilmington, Mass.) are lightly anesthetized with halothane, decapitated and the brains quickly removed to ice-cold, oxygenated medium (95% $O_2$/5% $CO_2$; 124 mM NaCl, 2 mM KCl, 1.25 mM $NaH_2PO_4$, 26 mM $NaHCO_3$, 10 mM d-glucose, 2 mM $MgSO_4 \cdot 7H_2O$ and 2 mM $CaCl_2$; pH 7.4). The ventral tegmental area is blocked and glued using cyanoacrylate to the stage of a Lancer Vibratome (Series 1000) filled with ice cold medium. Coronal slices (350 $\mu$) are cut and placed in oxygenated medium (22° C.) for 1 hour prior to recording. For recording, slices are placed on a nylon net in a recording chamber where they are completely submerged in continually flowing medium at 35° C. (~1 ml/min). All drugs are applied by switching the perfusion medium to a solution containing the drug. Spontaneous extracellular action potentials are recorded using 0.9% saline-filled glass pipettes (6–8 MW). Firing rates are plotted on-line in bins of 10 or 20 seconds and alterations in firing rate are calculated using average rates over 2 min epochs before and after drug application. Concentration-response curves are constructed and analyzed by linear regression.

(3) Microdialysis

I shaped concentric microdialysis probes are constructed out of dialysis fiber (molecular weight cut off of 18,000, 300 um o.d., Hospal, The Netherlands) occluded at one end with epoxy resin and attached to fused silica microtubing. The probes, 9 mm long with 2 mm length of exposed dialysis membrane are implanted into the nucleus accumbens (AP 1.7, ML −1.2, DV −8.0) of male Sprague Dawley rats (300–350g) anesthetized with ketamine (75 mg/kg) and xylazine (10 mg/kg). Following surgery, rats are placed in perspex cages inside insulation boxes and the probe inlets connected via flexible PEEK tubing through a dual channel fluid swivel system to a CMA/100 microinfusion pump (CMA/Microdialysis, Acton, Mass.). The probe is perfused overnight with artificial cerebrospinal fluid (147 mM $NaCl_2$, 2.7 mM KCl, 1.3 mM $CaCl_2$, 1.0 mM $MgCl_2$ and 0.1 mM ascorbic acid) at 0.5 ml/min. The next day, an experiment is started by increasing the flow to 1.5 ml/min and connecting the probe outlet with PEEK tubing to a 30 ml sample loop in a DECADE electrochemical detector (ANTEC, Leiden, The Netherlands). Microdialysis samples (30 ml) are collected on-line and automatically injected onto the column every 20 or 25 min. Analytes are separated at 35° C. over a BDS Hypersil $C_{18}$ 3 m column (150×3 mm) by reverse phase HPLC using a 75 mM potassium phosphate mobile phase of pH 5.0, containing 0.8 mM octanesulfonate, 8% methanol, 3 mM triethylamine and delivered at a flow rate of 0.35 ml/min by an ESA 580 pump. Amperometric detection of dopamine is performed using a glassy carbon electrode of the DECADE detector set at 550 mV vs Ag/AgCI. Extracellular levels of dopamine are quantified by comparing peak heights with those of standards.

After obtaining a stable baseline (5–7 samples collected every 20 or 25 min) drugs are administered and release of DA monitored for 4 to 7 hours. Dialysate concentrations are expressed as a percentage of baseline. Dialysate concentrations of DA are not corrected for recovery across the dialysis fiber. To determine whether each dose of drug has a significant effect on nucleus accumbens DA release multivariate analysis of variance with repeated measures over time is performed using SuperANova software (Abacus Concepts, Inc. Berkeley Calif.)

The ability of a particular compound to exhibit an anti-Parkinsonian effect in nonhuman primates can be determined using the procedures described by Greenemyre et al., Ann. Neurol., 35:655–661, 1994, and Klockgether et al., Ann. Neurol., 30:717–723, 1991.

The agonist and antagonist activities of a particular compound of the invention at 5-$HT_{1A}$ receptors can be determined using a single saturating concentration according to the following procedure. Male Hartley guinea pigs are decapitated and 5-$HT_{1A}$ receptors are dissected out of the hippocampus. The individual tissues are homogenized in 5 mM HEPES buffer containing 1 mM EGTA (pH 7.5) using a hand-held glass-Teflon® homogenizer and centrifuged at 35,000× g for 10 minutes at 4° C. The pellets are resuspended in 100 mM HEPES buffer containing 1 mM EGTA (pH 7.5) to a final protein concentration of 20 mg (hippocampus) or 5 mg (substantia nigra) of protein per tube. The following agents are added so that the reaction mix in each tube contained 2.0 mM $MgCl_2$, 0.5 mM ATP, 1.0 mM cAMP, 0.5 mM IBMX, 10 mM phosphocreatine, 0.31 mg/mL creatine phosphokinase, 100 mM GTP and 0.5–1 microcuries of [$^{32}$P]-ATP (30 Ci/mmol: NEG-003 —New England Nuclear). Incubation is initiated by the addition of tissue to siliconized microfuge tubes (in triplicate) at 30° C. for 15 minutes. Each tube receives 20 mL tissue, 10 mL drug or buffer (at 10×final concentration), 10 mL 32 nM agonist or buffer (at 10×final concentration), 20 mL forskolin (3 mM final concentration) and 40 mL of the preceding reaction mix. Incubation is terminated by the addition of 100 mL 2% SDS, 1.3 mM cAMP, 45 mM ATP solution containing 40,000 dpm [$^3$H]-cAMP (30 Ci/mmol: NET-275 —New England Nuclear) to monitor the recovery of cAMP from the columns. The separation of [$^{32}$P]-ATP and [$^{32}$P]-cAMP is accomplished using the method of Salomon et al., *Analytical Biochemistry*, 1974, 58, 541–548. Radioactivity is quantified by liquid scintillation counting. Maximal inhibition is defined by 10 mM (R)-8-OH-DPAT for 5-HT$_{1A}$ receptor. Percent inhibition by the test compound is then calculated in relation to the inhibitory effect of (R)-8-OH-DPAT. The reversal of agonist induced inhibition of forskolin-stimulated adenylate cyclase activity is calculated in relation to the 32 nM agonist effect.

This invention relates both to methods of treating Parkinson's disease and ADHD in which the two or three active agents employed are administered together, as part of the same pharmaceutical composition, as well as to methods in which these active agents are administered separately as part of an appropriate dose regimen designed to obtain the benefits of the combination therapy. The appropriate dose regimen, the amount of each dose administered, and specific intervals between doses of each active agent will depend upon the subject being treated, how well tolerated the drug is and the severity of the condition. Generally, in carrying out the above combination methods of this invention, the 5HT$_{1A}$ receptor agonist will be administered in an amount ranging from about 5–90 mg per day, in single or divided doses, the $\alpha_2$ adrenergic receptor ligand will be administered in an amount ranging from about 1.0–100 mg per day, in single or divided doses, in the case of an $\alpha_2$ adrenergic receptor antagonist, and in an amount ranging from about 0.1–100 mg per day, in single or divided doses, in the case of an $\alpha_2$ adrenergic receptor agonist, in single or divided doses, and the D2 receptor agonist will be administered in an amount ranging from about 0.5 mg –25 mg per day, in single or divided doses. (For FDA approved drugs that are used in the combination methods of this invention, physicians will be guided by the dosage ranges for such drugs that are specified in the Physician's Desk Reference). Variations may nevertheless occur depending upon the species of animal being treated and its individual response to said medicament, as well as on the type of pharmaceutical formulation chosen and the time period and interval at which such administration is carried out. In some instances, dosage levels below the lower limit of the aforesaid range may be more than adequate, while in other cases still larger doses may be employed without causing any harmful side effect, provided that such larger doses are first divided into several small doses for administration throughout the day.

The combination methods of this invention include methods wherein the desired combined activities are present in one compound or pharmaceutically acceptable salt. The pharmaceutical compositions of this invention that exhibit more than one pharmaceutical activity (e.g., 5HT$_{1A}$ agonism and D2 agonism) include those pharmaceutical compositions wherein all the desired pharmaceutical activities are present in one compound or pharmaceutically acceptable salt.

The D2 receptor agonists, the 5HT$_{1A}$ receptor agonists, and the $\alpha_2$ receptor antagonists that are employed in the pharmaceutical compositions and methods of this invention are hereinafter also referred to as "therapeutic agents". The therapeutic agents can be administered via either the oral or parenteral route. Compositions containing both a D2 receptor agonist and a 5HT$_{1A}$ receptor agonist, or all three of a D2 receptor agonist, a 5HT$_{1A}$ receptor agonist and an $\alpha_2$ adrenergic receptor antagonist, will generally be administered orally or parenterally daily, in single or divided doses, so that the total amount of each active agent administered falls within the above guidelines.

The therapeutic agents may be administered alone or in combination with pharmaceutically acceptable carriers or diluents by either of the routes previously indicated, and such administration may be carried out in single or multiple doses. More particularly, the therapeutic agents of this invention can be administered in a wide variety of different dosage forms, i.e., they may be combined with various pharmaceutically acceptable inert carriers in the form of tablets, capsules, lozenges, troches, hard candies, suppositories, aqueous suspensions, injectable solutions, elixirs, syrups, and the like. Such carriers include solid diluents or fillers, sterile aqueous media and various non-toxic organic solvents, etc. Moreover, oral pharmaceutical compositions can be suitably sweetened and/or flavored. In general, the therapeutic compounds of this invention, when administered separately (i.e., not in the same pharmaceutical composition) are present in such dosage forms at concentration levels ranging from about 5.0% to about 70% by weight.

For oral administration, tablets containing various excipients such as microcrystalline cellulose, sodium citrate, calcium carbonate, dicalcium phosphate and glycine may be employed along with various disintegrants such as starch (and preferably corn, potato or tapioca starch), alginic acid and certain complex silicates, together with granulation binders like polyvinylpyrrolidone, sucrose, gelatin and acacia. Additionally, lubricating agents such as magnesium stearate, sodium lauryl sulfate and talc are often very useful for tabletting purposes. Solid compositions of a similar type may also be employed as fillers in gelatin capsules; preferred materials in this connection also include lactose or milk sugar as well as high molecular weight polyethylene glycols. When aqueous suspensions and/or elixirs are desired for oral administration, the active ingredient may be combined with various sweetening or flavoring agents, coloring matter or dyes, and, if so desired, emulsifying and/or suspending agents as well, together with such diluents as water, ethanol, propylene glycol, glycerin and various like combinations thereof.

For parenteral administration, solutions of a therapeutic agent in either sesame or peanut oil or in aqueous propylene glycol may be employed. The aqueous solutions should be suitably buffered if necessary and the liquid diluent first rendered isotonic. These aqueous solutions are suitable for intravenous injection purposes. The oily solutions are suitable for intraarticular, intramuscular and subcutaneous injection purposes. The preparation of all these solutions under sterile conditions is readily accomplished by standard pharmaceutical techniques well known to those skilled in the art.

The following example is intended only to illustrate the invention, and not to be interpreted as limiting its scope.

EXAMPLE

The behavioral effects of administration of sunipetron on parkinsonian score in MPTP-(1-methyl-4-phenyl-1,2,3,6-tetrahydropyridine) treated monkeys was determined. The methods employed are described in Greenemyre et al., supra and Klockgether et al., supra.

Briefly, parkinsonian monkeys were administered 0.5 mg/kg or 1.0 mg/kg of sunipetron and the severity of parkinsonian symptoms was rated at each of 4 time points after drug administration as compared with administration of a control solution ("Vehicle").

Parkinsonian scores obtained from the study are shown in FIG. 1. Combined with the estimates shown for plasma levels of the compound following administration, the data demonstrate that the maximum reduction in parkinsonian score was attained at plasma levels of approximately 200 ng/ml. The minimum effective plasma level was approximately 100 ng/ml.

What is claimed is:

1. A method of treating a disorder selected from Parkinson's Disease, ADHD, or microadenomas in a mammal, comprising administering to a mammal in need of such treatment an amount of a compound of the formula

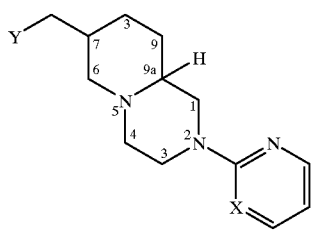

I or a pharmaceutically acceptable acid addition salt thereof, wherein

X is selected from N or CH;

Y is selected from

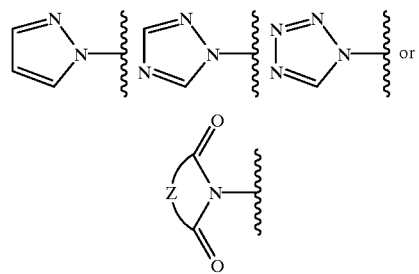

Z is selected from

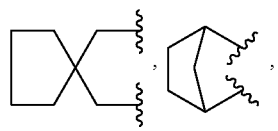

$SCH_2$, $OCH_2$, $Y^1(CH_2)_n$ or $Y^1(CH_2)_n$ substituted on carbon with up to 2 methyl groups;

n is 1 or 2; and $Y^1$ is selected from $CH_2$, NH or $NCH_3$;

that is effective in treating such disorder.

2. A method according to claim 1 wherein the compound of formula (I) or pharmaceutically acceptable salt that is employed is one wherein Y is

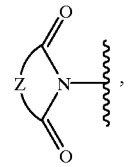

Z is $Y^1(CH_2)_n$, $Y^1$ is $CH_2$, n is 1 and X is N.

3. A method according to claim 1 of treating Parkinson's disease in a mammal, comprising administering to a mammal in need of such treatment an amount of sunipetron, or a pharmaceutically acceptable salt thereof, that is effective in treating Parkinson's Disease.

4. A method according to claim 1 of treating ADHD in a mammal, comprising administering to a mammal in need of such treatment an amount of sunipetron, or a pharmaceutically acceptable salt thereof, that is effective in treating ADHD.

5. A method according to claim 1 of treating microadenomas in a mammal, comprising administering to a mammal in need of such treatment an amount of sunipetron, or pharamaceutically acceptable salt thereof, that is effective in treating microadenomas.

* * * * *